United States Patent
Modi

(10) Patent No.: US 6,979,668 B2
(45) Date of Patent: Dec. 27, 2005

(54) CLEANING COMPOUND FOR AND METHOD OF CLEANING VALVES AND ACTUATORS OF METERED DOSE DISPENSERS CONTAINING PHARMACEUTICAL COMPOSITIONS

(75) Inventor: Pankaj Modi, Ancaster (CA)

(73) Assignee: Generex Pharmaceuticals Incorporated, Toronto (CA)

( * ) Notice: Subject to any disclaimer, the term of this patent is extended or adjusted under 35 U.S.C. 154(b) by 234 days.

(21) Appl. No.: 10/320,045

(22) Filed: Dec. 16, 2002

(65) Prior Publication Data

US 2004/0116318 A1 Jun. 17, 2004

(51) Int. Cl.$^7$ ............................. C11D 9/36; C11D 3/18
(52) U.S. Cl. ................. 510/161; 510/432; 510/439; 510/466; 128/200.13; 128/200.21
(58) Field of Search .................... 128/200.13, 200.21; 510/161, 432, 439, 466

(56) References Cited

U.S. PATENT DOCUMENTS

| | | | |
|---|---|---|---|
| 2,993,866 A | | 7/1961 | Vaughn et al. |
| 3,342,740 A | | 9/1967 | Kazmierczak et al. |
| 3,873,686 A | * | 3/1975 | Beekman ..................... 424/47 |
| 3,903,258 A | * | 9/1975 | Siegal ......................... 424/66 |
| 4,113,852 A | * | 9/1978 | Kenkare et al. .............. 424/46 |
| 4,880,557 A | | 11/1989 | Ohara et al. |
| 4,902,499 A | * | 2/1990 | Bolish et al. ............. 424/70.12 |
| 4,983,418 A | * | 1/1991 | Murphy et al. ................ 424/47 |
| 5,203,323 A | * | 4/1993 | Tritle ..................... 128/200.23 |
| 5,286,476 A | * | 2/1994 | Nanba et al. .................. 424/47 |
| 5,483,954 A | * | 1/1996 | Mecikalski ............. 128/203.15 |
| 5,536,444 A | | 7/1996 | Hettche et al. |
| 5,604,189 A | | 2/1997 | Zhang et al. |
| 6,415,785 B1 | * | 7/2002 | Stage ..................... 128/200.23 |
| 6,431,168 B1 | * | 8/2002 | Rand et al. ............. 128/200.23 |
| 6,702,155 B1 | * | 3/2004 | Rebne ........................ 222/207 |

OTHER PUBLICATIONS

John J. Sciarra, PH.D. and Anthony J. Cutie, PH.D., Aerosols, Chapter 93, pp. 1662-1677.

* cited by examiner

Primary Examiner—Charles Boyer
(74) Attorney, Agent, or Firm—Hamilton, Brook, Smith & Reynolds, P.C.

(57) ABSTRACT

A method of cleaning a metered dose spray device, and a cleaning composition for such cleaning, prevent the device from becoming clogged with medication. The method includes removing the aerosol can containing the medication from the actuator, placing an aerosol can containing a cleaning composition in the actuator, and dispensing the cleaning solution through the actuator. The residual medication is thereby removed from the actuator. A sufficiently small quantity of cleaning composition remains in the actuator so that the cleaning composition itself will not clog the actuator. Additionally, the cleaning composition is non-toxic, so that residual cleaning composition remaining in the actuator will not harm the user when a subsequent dose of medication is dispensed.

7 Claims, 4 Drawing Sheets

CLEANING COMPOUND FOR AND METHOD OF CLEANING VALVES AND ACTUATORS OF METERED DOSE DISPENSERS CONTAINING PHARMACEUTICAL COMPOSITIONS

BACKGROUND OF THE INVENTION

1. Field of the Invention

The present invention relates to a method of cleaning actuators of metered dose dispensers used to dispense pharmaceutical compositions. The invention also relates to a composition to be used in cleaning actuators of metered dose dispensers.

2. Description of the Related Art

Metered dose spray devices are presently used to administer many different medications to the mouth and lungs, for example, asthma medication and nitroglycerin for treatment of heart disease. A typical metered dose spray device includes a container, for example, a can, for containing a solution or suspension of medication, a metering valve, and an actuator. The can will contain the medication to be dispensed, possibly a solvent for the medication, and a propellant. The propellant is a substance having a low boiling point and high vapor pressure, so that as liquid is dispensed from the container the propellant evaporates, thereby maintaining a constant pressure within the can. Actuation of the metering valve causes the metering chamber within the valve to close with respect to the can's interior, and open with respect to the mouthpiece (the structure of the actuator to be positioned in communication with the user's mouth). Propellant within the metering chamber will evaporate due to the sudden decrease in pressure when the valve is actuated, propelling the medication into the user's mouth.

After repeated use, the actuator can become clogged with the medication being dispensed. This can interfere with proper dosing and delivery of the medication. It is desirable, therefore, to provide a method of cleaning the actuator on a regular basis to resist clogging and assure delivery of the desired amount of medication.

SUMMARY OF THE INVENTION

The present invention provides a method of cleaning an actuator of a metered dose dispenser containing a pharmaceutical product, and also provides a chemical composition for performing this cleaning.

Generally, the metered dose spray device consists of three major components; an aerosol container (which in many preferred embodiments will be a can) containing medication in liquefied propellant gas; a metering valve, which when depressed dispenses a known quantity of the medication; and a buccal spray actuator which when combined with the stem of the metering valve comprises an expansion chamber, also called a sump, and a nozzle, often called a spray orifice. The actuator itself is comprised of an actuator boot, stem block, sump, spray orifice and mouthpiece. The actuator boot keeps the aerosol can fixed in place. The stem block is dimensioned and configured to receive the stem of the metering valve, which is fixed to the aerosol can, and whose purpose is to carry the medication from the metering valve to the actuator sump, specially designed to act as an expansion chamber and to redirect the aerosol through the spray orifice.

In the rest position, the metering chamber of the valve is connected directly to the aerosol can containing the medication, permitting free flow from the metering chamber to the container. The vapor pressure of the propellant therefore ensures that the metering chamber remains full of the medication/propellant mixture, and the capillary action of the passage from the container to the metering chamber prevents fluid in the metering chamber from exiting back into the container. Upon depression of the can towards the actuator, the valve stem is pushed into the can. The connection between the aerosol container and metering chamber is thereby closed and the metered discharge process begins. The metered dose is ejected from the metering chamber under the pressure of the flashing liquid propellant. The medication then passes through the valve stem orifice into the actuator sump where it undergoes further boiling as it attempts to fill the chamber and displace the air. Finally, a high-quality spray, particularly suited to buccal delivery, emerges from the spray orifice and mouthpiece of the actuator.

Cleaning is performed by first removing the aerosol can containing the medication, and replacing it with an aerosol container or can containing a cleaning composition. The cleaning composition's can is then depressed towards the actuator to force the valve stem into the container and discharge the cleaning composition through the actuator's sump and orifice. Residue of the pharmaceutical product present in the actuator is substantially removed by the discharge of the cleaning composition therethrough, by the force of the flowing cleaning composition and/or by being dissolved in a solvent within the cleaning composition.

A cleaning composition, to be used in the above method, is also provided in the present invention. The cleaning composition is itself non-toxic and leaves little or no residue in the actuator, and thus does not interfere with subsequent delivery of the pharmaceutical product. The cleaning composition is preferably comprised of silicone and a propellant, and optionally, an organic solvent.

It is therefore an object of the present invention to provide a method of cleaning an actuator of a metered dose spray device used in delivery of pharmaceutical agents.

It is another object of the present invention to provide a cleaning composition for preventing clogs within the actuator of a metered dose spray device.

It is a further object of the present invention to provide an efficient and economical method of cleaning a metered dose spray device.

It is another object of the present invention to provide an apparatus for cleaning a metered dose spray device that is easy to use.

It is a further object of the present invention to provide a safe cleaning composition for use with metered dose spray devices.

These and other objects of the present invention will become more apparent through the following description and drawings.

BRIEF DESCRIPTION OF THE DRAWINGS

Like reference numbers denote like elements throughout the drawings.

DETAILED DESCRIPTION

The present invention provides a method of cleaning a metered dose spray device, and a chemical composition for performing this cleaning.

Referring to the figures, the metered dose spray device 10 includes an actuator 12, an aerosol can 14, and a metering valve 16.

Figure 2:
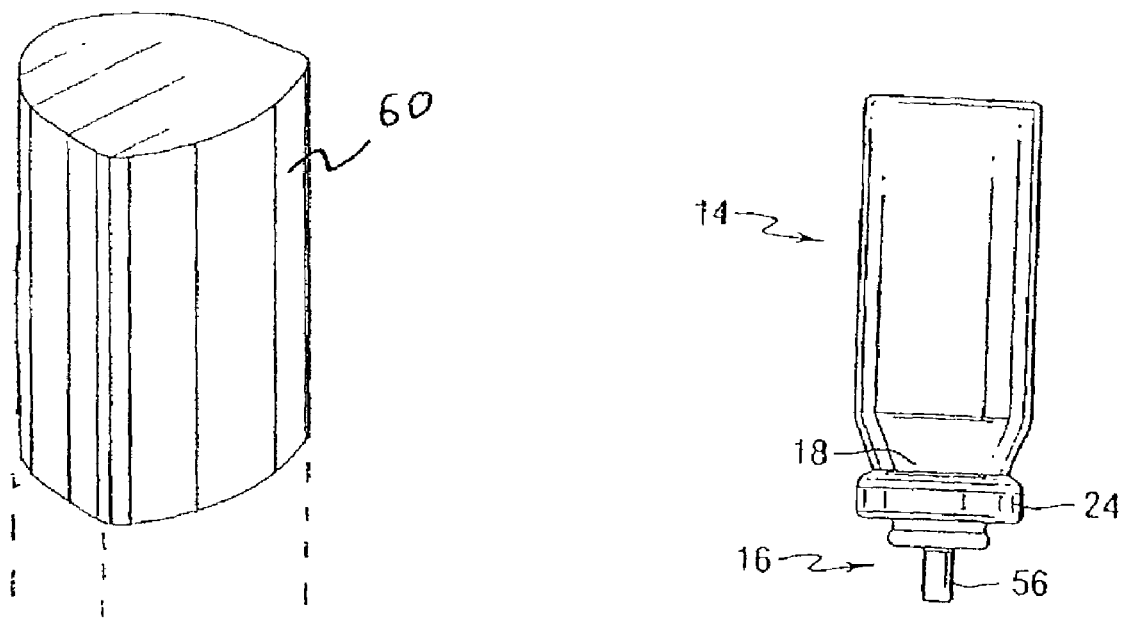
FIG. 2 is a side view of a can and metering valve assembly for a metered dose spray device.
Figure 3:
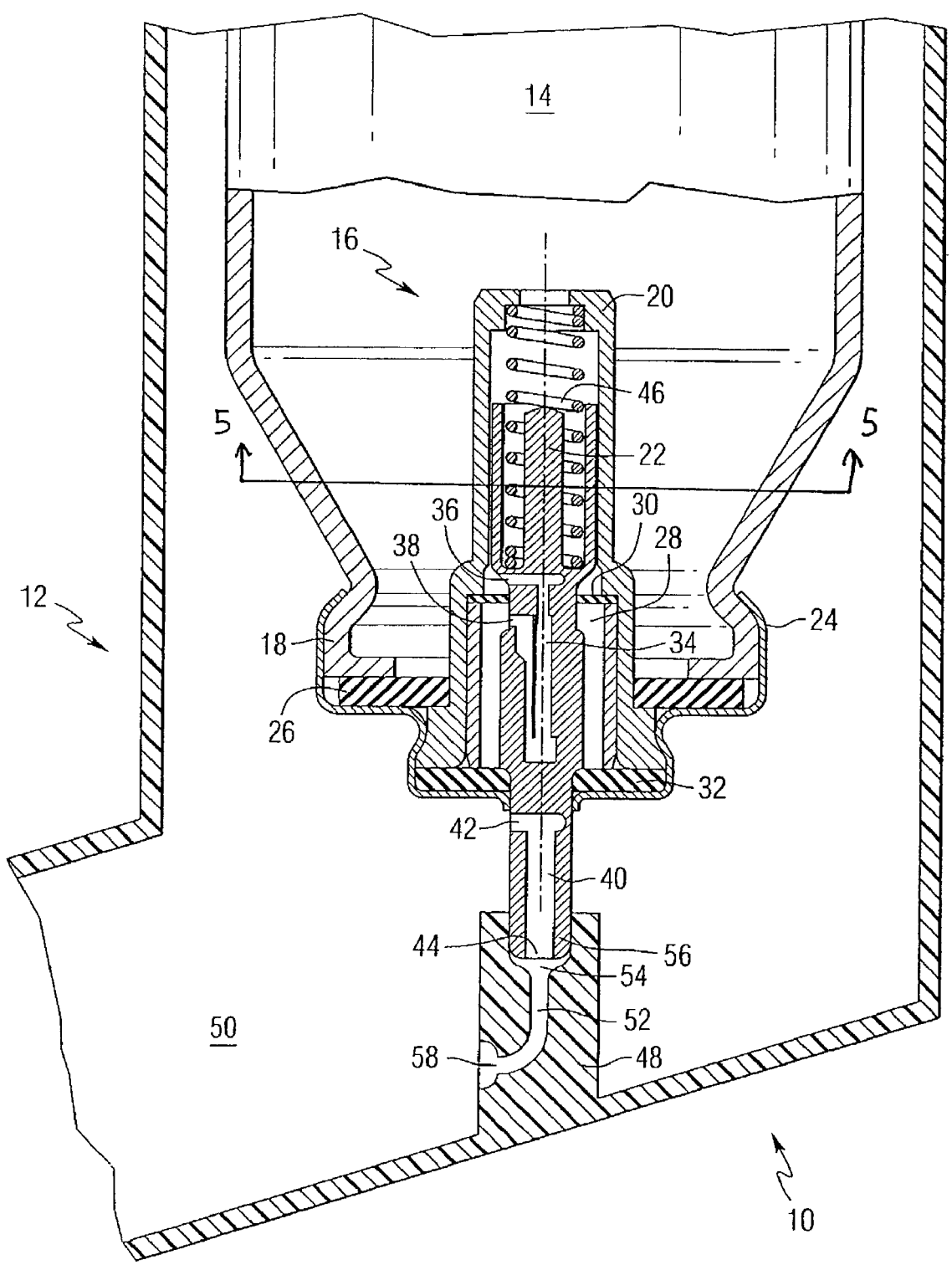
FIG. 3 is a cross-sectional side view of an actuator, can and metering valve for a metered dose spray device showing the metering valve closed.
Figure 4:
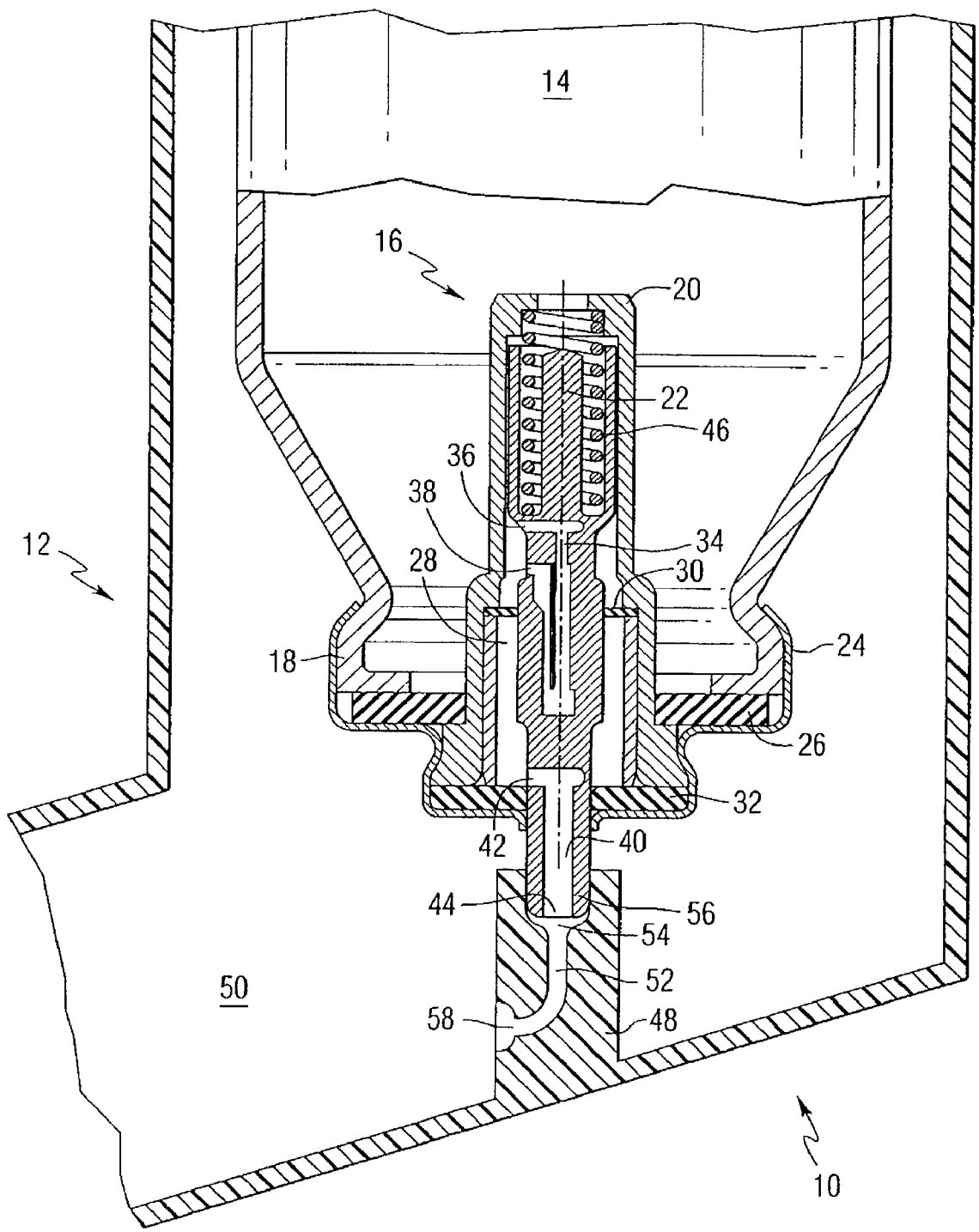
FIG. 4 is a side cross-sectional view of an actuator, can and metering valve for a metered dose spray device showing the metering valve open.

The aerosol can 14 is best illustrated in FIGS. 2–4. The aerosol can 14 is preferably cylindrical having an open end 18. The open end 18 is dimensioned and configured to mate with the ferrule (described below) of the metering valve 16. A preferred material for the can 14 is aluminum, but stainless steel or other suitable materials can also be used.

Figure 5:
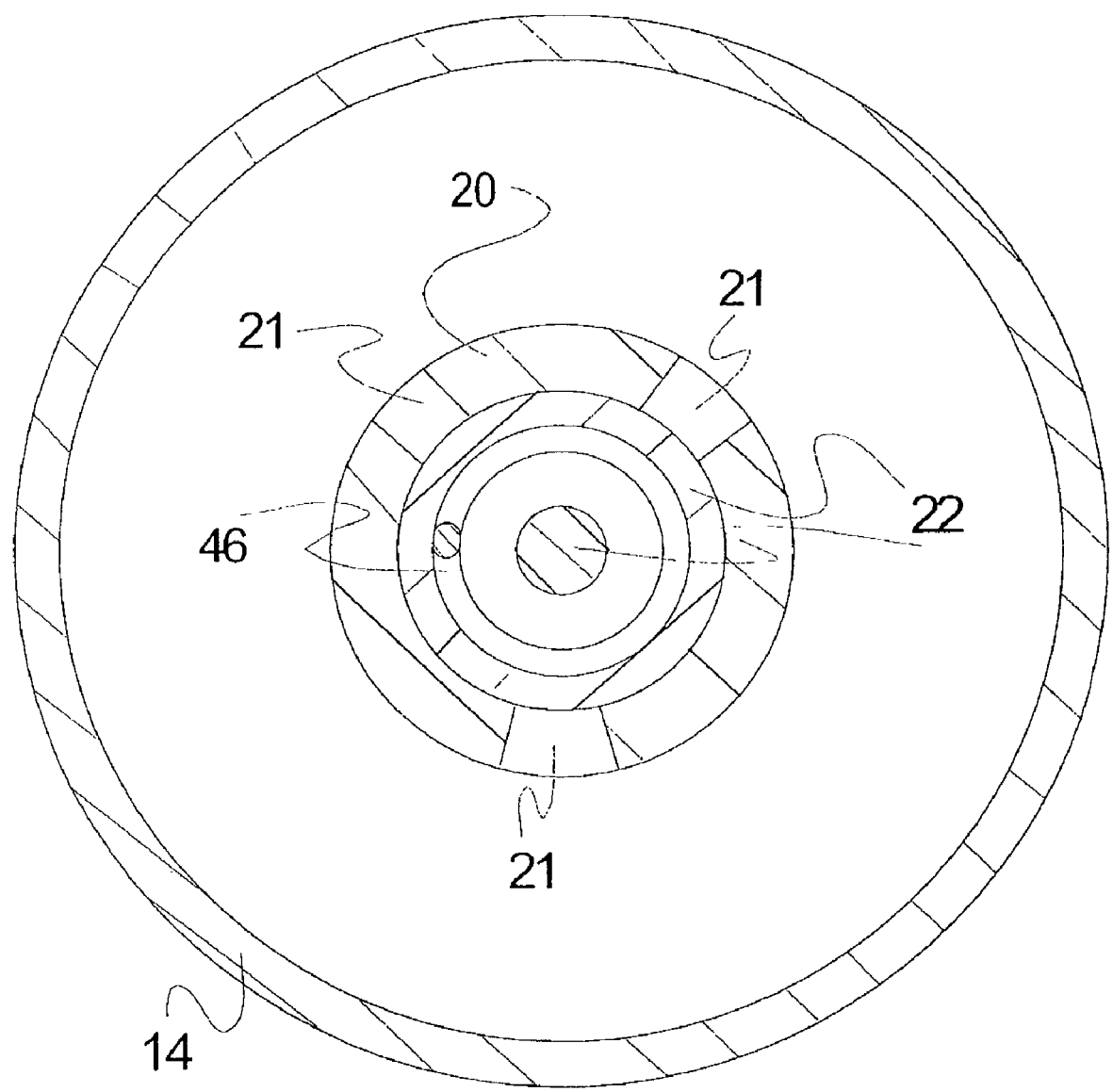
FIG. 5 is a cross-sectional view of a can and valve assembly, taken along the lines 5—5 in FIG. 3.

Referring to FIGS. 3–4, the metering valve 16 includes a housing 20, having a plurality of slots 21 (FIG. 5) with a stem 22 slidably contained therein. A preferred material for the 3-slot housing and stem is polyester, but acetyl resins or other suitable materials can be used as well. The metering valve 16 also includes a ferrule 24, dimensioned and configured to fit around the outside of the open end 18 of the aerosol can 14, being crimped around the end 18 to secure the metering valve 16 to the can 14. A preferred material for the ferrule is aluminum. A sealing gasket 26 provides a seal between the can's open end 18 and the ferrule 24. A preferred material for the sealing gasket 26 is nitrile (buna) rubber. A metering chamber 28 within the 3-slot housing 20 is defined between the upper annular stem gasket 30 and the lower annular stem gasket 32. A preferred material for the first and second stem gaskets 30,32 is nitrile (buna) rubber. The stem 22 includes an upper stem and a lower stem, with the lower stem having a U-shaped retention channel 34 having ends 36 and 38, and an upper stem having a channel 40 having ends 42 and 44. The principle of retention lies in the particular geometry at the base of the stem 22, which allows the passage of the fluid under the differential pressure from the aerosol can 14 to valve metering chamber 28 after actuation, but resists the return (due to gravity) of the fluid to the aerosol can 14 by the capillary action of the retention channel 34.

The stem 22 moves between the rest (closed) position and an open position. Within the rest position, shown in FIG. 3, the inlet end 36 of the retention channel 34 is above the first stem gasket 30, so that the contents of the aerosol can 14 may enter the retention channel 34. The outlet end 38 of the retention channel 34 is below the first stem gasket 30 and within the metering chamber 28. Both the inlet end 42 and outlet end 44 of the channel 40 are outside the metering chamber 28, thereby resisting passage of fluid from the metering chamber 28 to the channel 40. In the open position, shown in FIG. 4, both the inlet end 36 and outlet end 38 of the retention channel 34 are above the first stem gasket 30 of the metering chamber 28, thereby resisting any fluid flow from the aerosol can 14 to the metering chamber 28. At the same time, the inlet end 42 of the channel 40 is above the second stem gasket 32 and inside the metering chamber 28, thereby permitting passage of fluid from the metering chamber 28 through the passage 40. The stem 22 is biased by the spring 46 into the rest position of FIG. 3.

Figure 1:
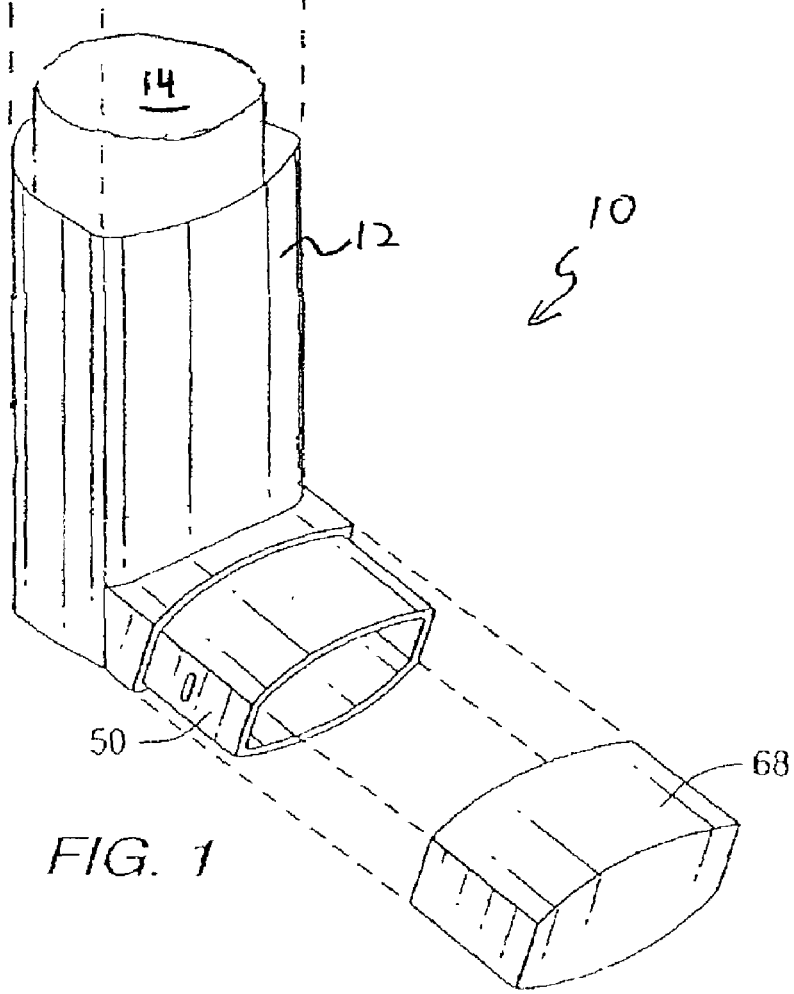
FIG. 1 is a front isometric view of a metered dose spray device.

The actuator 12 is best illustrated in FIGS. 1, 3 and 4. The actuator 12 includes mouthpiece 50, a stem block 48 and an actuator sump 52. The actuator sump 52, which is located in the stem block 48, includes an inlet end 54, dimensioned and configured to receive the lower end 56 of the valve stem 22, and an outlet end 58, called a spray orifice. The spray orifice 58 of the actuator sump 52 is dimensioned and configured to direct medication towards the back of the throat. The spray orifice 58 may have a generally round configuration. The sump volume is preferably sufficient to generate a high-pressure stream of fluid upon actuation of the metered dose spray device.

The actuator 12 may also include a cap 60, surrounding the actuator 12 and aerosol can 14. The cap 60 is preferably slidably and removably secured to the actuator 12. One method of slidably and removably securing the cap 60 to the actuator 12 is by friction, thereby permitting removal or reattachment of the cap 60 and actuator 12 by merely pulling upward on the cap 60. The actuator 12 may also include a dust cover 68, dimensioned and configured to cover the mouthpiece 50.

The cleaning composition of the present invention include a mixture of silicone and an appropriate propellant, and may optionally include an organic solvent. Preferably, silicone is about 1–10 wt./wt. % of the total cleaning composition, and propellant is about 90–99 wt./wt. % of the cleaning composition.

Propellants commonly used in conjunction with drug delivery via metered dose spray devices are also appropriate for use with the present cleaning composition. Such propellants include tetrafluoroethane, heptafluoroethane, dimethylfluoropropane, tetrafluoropropane, butane, isobutane, dimethyl ether and other non-CFC and CFC propellants. The preferred propellants are hydrogen-containing chlorofluorocarbons, hydrogen-containing fluorocarbons, dimethyl ether and diethyl ether. Even more preferred is HFA-134a (1,1,1,2-tetrafluoroethane).

Suitable organic solvents for use with the cleaning composition of the present invention include alcohol solutions, such as ethanol.

Use of the metered dose spray device 10 begins with the valve 16 in its rest position. When the valve 16 is in its rest position as shown in FIG. 4, medication within the aerosol can 14 is free to move through the slots 21 within the metering valve's housing 20, through the U-shaped retention channel 34, and into the metering chamber 28. The propellant, specifically selected for its high vapor pressure, evaporates to the maximum extent permitted by the volume of the aerosol can 14. The medication within the aerosol can 14 is thereby forced through the retention channel 34 until the metering chamber 28 is full. The elongated and curved shape of the retention channel 34 keeps the medication in the metering channel 28 from traveling back into the aerosol can 14. The location of the channel 40 below the second stem gasket 32 resists medication from exiting the metering chamber 28 prematurely.

To use the metered dose spray device 10, the lower end 56 of the stem 22 is first inserted into the inlet end 54 of the actuator sump 52, located in the stem block 48 of the actuator 12. The cap 60 may also be secured to the actuator 12, thereby completely concealing the aerosol can 14. The dust cover 68 is removed from the mouthpiece 50. The mouthpiece 50 is inserted into the user's mouth and the aerosol can 14 (possibly along with the cap 60) is depressed towards the actuator 12. This action causes the metering valve 16 to move from its rest position of FIG. 3 to its open position of FIG. 4. When the stem 22 is moved from the rest position of FIG. 3 to the open position shown in FIG. 4, the outlet opening 38 of the retention channel 34 is moved above the first stem gasket 30, thereby resisting medicine from moving from the aerosol can 14 to the metering chamber 28. At the same time, the inlet end 42 of the channel 40 is brought above the second stem gasket 32, thereby providing a path from the metering chamber 28, through the channel 40 and actuator sump 52, spray orifice 58, through the mouthpiece 50, and into the user's mouth. Opening the metering valve 16 also decreases the pressure within the metering chamber 28, causing the propellant in the metering chamber 28 to evaporate, thereby pushing the medication out through the channel 40 into the actuator sump 52, where it undergoes further evaporation as it attempts to fill the chamber and displace the air, and finally through spray orifice 58 and out the mouthpiece 50. Releasing downward pressure on the aerosol can 14 causes the metering valve 16 to return to its rest position under pressure from the spring 46, thereby permitting a new dosage of medication to enter the metering chamber through the retention channel 34, under pressure from the evaporated propellant within the aerosol can 14.

To clean the actuator 12 of the metered dose spray device 10, the cap 60 is first removed. The can 14 containing the medication is then removed, and is replaced with another can 14 containing the cleaning composition. As before, the lower end 56 of the stem 22 is inserted into the inlet end 54 of the actuator sump 52, located in the stem block 48 of the actuator 12. The dust cover 68 should remain removed from the mouthpiece 50. The aerosol can 14 containing the cleaning composition is depressed towards the actuator 12. This action causes the metering valve 16 to move from its rest position of FIG. 3 to its open position of FIG. 4. When the stem 22 is moved from the rest position of FIG. 3 to the open position shown in FIG. 4, the outlet opening 38 of the retention channel 34 is moved above the first stem gasket 30, thereby resisting cleaning composition from moving from the aerosol can 14 to the metering chamber 28. At the same time, the inlet end 42 of the channel 40 is brought above the second stem gasket 32, thereby providing a path from the metering chamber 28, through the channel 40 and actuator sump 52, spray orifice 58, and through the mouthpiece 50. Opening the metering valve 16 also decreases the pressure within the metering chamber 28, causing the propellant in the metering chamber 28 to evaporate, thereby pushing the cleaning composition out through the channel 40 into the actuator sump 52, where it undergoes further evaporation as it attempts to fill the chamber and displace the air, and finally through the spray orifice 58 and out the mouthpiece 50. As the cleaning composition passes through the various portions of the actuator 12, it carries with it any remaining medication within the actuator 12, thereby preventing any clogs within the actuator sump 52. Releasing downward pressure on the aerosol can 14 causes the metering valve 16 to return to its rest position under pressure from the spring 46, thereby permitting a new supply of cleaning composition to enter the metering chamber through the retention channel 34, under pressure from the evaporated propellants within the aerosol can 14. Upon completion of cleaning, the aerosol can 14 containing the cleaning composition should immediately be replaced with the aerosol can 14 containing the medication. The cap 60 may again be placed on the actuator 12, so that the metered dose spray device 10 is ready to administer the next dose of medication.

While a specific embodiment of the invention has been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of cleaning an actuator of an aerosol metered dose dispenser containing a pharmaceutical product, comprising:
   replacing the canister containing the pharmaceutical product with a canister containing a cleaning composition; and
   discharging the cleaning canister at least one time after discharge of the pharmaceutical product so that the pharmaceutical product residue present in the actuator is substantially removed by the discharge of the cleaning composition therethrough.

2. The method of claim 1, wherein said cleaning composition is comprised of a propellant and silicone.

3. The method of claim 2, wherein said propellant is selected from the group consisting of tetrafluoroethane, heptafluoroethane, dimethylfluoropropane,, tetrafluoropropane, butane, isobutane, diethyl ether, hydrogen-containing chlorofluorocarbons, hydrogen-containing chlorofluorocarbons, hydrogen-containing fluorocarbons, and diethyl ether.

4. The method of claim 2, wherein the propellant is present in a concentration of about 90 to 99 wt./wt. % of the total cleaning composition and the silicone is present in a concentration of about 1 to 10 wt./wt. % of the total cleaning composition.

5. The method of claim 2, further comprising an organic solvent.

6. The method of claim 5, wherein the organic solvent is selected from the group consisting of alcohol solutions and ethanol an alcohol solution.

7. The method of claim 6, wherein the alcohol solution is ethanol.

* * * * *